United States Patent
Shindo

(10) Patent No.: US 9,679,371 B2
(45) Date of Patent: Jun. 13, 2017

(54) PATTERN SHAPE EVALUATION DEVICE AND METHOD

(71) Applicant: Hitachi High-Technologies Corporation, Minato-ku, Tokyo (JP)

(72) Inventor: Hiroyuki Shindo, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/898,973

(22) PCT Filed: May 7, 2014

(86) PCT No.: PCT/JP2014/062242
§ 371 (c)(1),
(2) Date: Dec. 16, 2015

(87) PCT Pub. No.: WO2014/208202
PCT Pub. Date: Dec. 31, 2014

(65) Prior Publication Data
US 2016/0189368 A1    Jun. 30, 2016

(30) Foreign Application Priority Data

Jun. 24, 2013 (JP) ................. 2013-131834

(51) Int. Cl.
*G06K 9/00* (2006.01)
*G06T 7/00* (2017.01)
(Continued)

(52) U.S. Cl.
CPC ............ *G06T 7/0006* (2013.01); *G06T 7/001* (2013.01); *G06T 7/13* (2017.01); *H01J 37/222* (2013.01);
(Continued)

(58) Field of Classification Search
CPC ......... G06T 7/0006; G06T 7/001; G06T 7/13; G06T 2207/10016; G06T 2207/10061;
(Continued)

(56) References Cited

U.S. PATENT DOCUMENTS

| 6,868,175 B1 | 3/2005 | Yamamoto et al. |
| 8,217,351 B2 * | 7/2012 | Toyoda ................... H01L 22/12 250/306 |

(Continued)

FOREIGN PATENT DOCUMENTS

| JP | 7-260699 A | 10/1995 |
| JP | 10-312461 A | 11/1998 |

(Continued)

OTHER PUBLICATIONS

International Search Report (PCT/ISA/210) issued in PCT Application No. PCT/JP2014/062242 dated Aug. 5, 2014 with English translation (five pages).

(Continued)

*Primary Examiner* — Mekonen Bekele
(74) *Attorney, Agent, or Firm* — Crowell & Moring LLP

(57) ABSTRACT

In order to enable the computation of a process window including an arbitrary exposure condition, the present invention comprises: a contour data extraction means for extracting contour data from captured images of a plurality of circuit patterns formed by altering exposure conditions for identical design layouts; a shape variation measurement means for measuring, on the basis of the plurality of sets of extracted contour data, the amount of shape deformation at each edge or local region of the circuit patterns; a variation model computation means for computing, on the basis of the measured amount of shape deformation, a variation model for the contour data of a circuit pattern or a shape corresponding to a prescribed exposure condition; and a process (Continued)

window computation means using the variation model to estimate the amount of shape variation of a circuit pattern or a shape corresponding to an arbitrary exposure condition with respect to a circuit pattern or a shape corresponding to an exposure condition specified by a reference exposure condition and compute a process window on the basis of the estimated amount of shape variation.

10 Claims, 6 Drawing Sheets

(51) Int. Cl.
*H01J 37/22* (2006.01)
*G06T 7/13* (2017.01)
*H01J 37/28* (2006.01)
*H01L 21/66* (2006.01)

(52) U.S. Cl.
CPC ............. *G01N 2223/6113* (2013.01); *G06T 2207/10016* (2013.01); *G06T 2207/10061* (2013.01); *G06T 2207/10144* (2013.01); *G06T 2207/30148* (2013.01); *H01J 37/28* (2013.01); *H01L 22/12* (2013.01)

(58) Field of Classification Search
CPC . G06T 2207/10144; G06T 2207/30148; H01J 37/222; H01J 37/28; G01N 2223/6113; H01L 22/12
USPC ............... 382/145, 129; 250/311; 716/129
See application file for complete search history.

(56) References Cited

U.S. PATENT DOCUMENTS

| | | | | |
|---|---|---|---|---|
| 8,355,562 | B2 * | 1/2013 | Toyoda | ............... G06K 9/00 382/147 |
| 8,872,106 | B2 * | 10/2014 | Nishihama | ............ H01J 37/26 250/306 |
| 2002/0038510 | A1 * | 4/2002 | Savareigo | .......... G01N 21/8851 29/846 |
| 2003/0015660 | A1 | 1/2003 | Shishido et al. | |
| 2005/0232066 | A1 * | 10/2005 | Ishibashi | ............. G06F 17/5036 365/189.03 |
| 2006/0045326 | A1 | 3/2006 | Toyoda et al. | |
| 2008/0050676 | A1 * | 2/2008 | Hoshino | ................ B82Y 10/00 430/296 |
| 2008/0245965 | A1 * | 10/2008 | Sugiyama | ............. B82Y 10/00 250/311 |
| 2009/0202139 | A1 | 8/2009 | Toyoda et al. | |
| 2009/0218491 | A1 | 9/2009 | Morokuma et al. | |
| 2009/0231424 | A1 | 9/2009 | Honda et al. | |
| 2013/0136335 | A1 * | 5/2013 | Toyoda | ................ G06K 9/6255 382/147 |
| 2013/0150998 | A1 | 6/2013 | Matsuoka et al. | |
| 2014/0189631 | A1 * | 7/2014 | Sakata | ................ G06F 17/5077 716/129 |

FOREIGN PATENT DOCUMENTS

| | | |
|---|---|---|
| JP | 11-288879 A | 10/1999 |
| JP | 2001-338304 A | 12/2001 |
| JP | 2002-6479 A | 1/2002 |
| JP | 2003-173948 A | 6/2003 |
| JP | 2006-66478 A | 3/2006 |
| JP | 2009-194051 A | 8/2009 |
| JP | 2009-206453 A | 9/2009 |
| WO | WO 2007/094439 A1 | 8/2007 |
| WO | WO 2012/029220 A1 | 3/2012 |

OTHER PUBLICATIONS

Japanese-language Written Opinion (PCT/ISA/237) issued in counterpart Japanese Application No. PCT/JP2014/062242 dated Aug. 5, 2014 (three pages).

Matsuoka et al., "New method of Contour based mask shape compiler", Society of Photo-Optical Instrumentation Engineers, Photomask Technology 2007, Proc. of SPIE, vol. 6730 (thirteen (13) pages).

* cited by examiner

PATTERN SHAPE EVALUATION DEVICE AND METHOD

TECHNICAL FIELD

The present invention relates to a device and a method for evaluating a pattern shape of a semiconductor pattern formed on a substrate.

BACKGROUND ART

In a semiconductor process, is used a method for measuring, with use of a critical dimension SEM (scanning electron microscope), test patterns manufactured on a silicon wafer by altering a dose amount and a focus value of an exposure apparatus to determine a dose range and a focus range for manufacturing a normal pattern. Such method is disclosed in PTL 1. The method is hereinbelow referred to as "a process window analysis." In a development stage, the process window analysis is used as a criterion of determining an exposure condition and selecting a photosensitive light-receiving resin (hereinbelow referred to as "a resist") to be applied on the silicon wafer. Also, results of the process window analysis are used for management in a mass production stage and are fed back to the exposure apparatus as needed.

In a recent semiconductor process, the pattern is densified, and the pattern shape is complicated. This makes it difficult to automatically set an optimal process window (e.g., the dose range and the focus range) for all pattern shapes and all pattern layouts in the conventional critical dimension SEM. Accordingly, for the pattern or part of this kind, a method for visually determining whether or not the pattern is a normal pattern and deriving a process window is employed.

To automate the process window analysis for the parts that are difficult to measure, quantification of the pattern shape is required. Examples of a method for evaluating the pattern shape include: methods for evaluating the pattern shape by using a design data of an electronic device as a reference pattern (PTL 2 to 5); a method for evaluating the pattern shape by using a pattern of a good device as a reference pattern (PTL 3); and a method for evaluating the pattern shape by generating a stable reference pattern (PTL 6).

CITATION LIST

Patent Literature

PTL 1: Publication of JP 11-288879 A
PTL 2: JP Application No. 6-49264
PTL 3: Publication of JP 10-312461 A
PTL 4: Publication of JP 2002-6479 A
PTL 5: Publication of JP 2001-338304 A
PTL 6: Publication of JP 2009-194051 A
PTL 7: Publication of JP 2006-66478 A

Non-Patent Literature

NPL 1: "R. Matsuoka, New method of Contour based mask shape compiler, SPIE Proc 6730-21, 2007.9.21"

SUMMARY OF INVENTION

Technical Problem

Since the methods disclosed in PTL 2 to 5 assume that the difference between a pattern shape on the design data and a pattern shape actually transferred on a wafer is small, evaluation of the pattern shape will be mistaken when the difference in shape is large. When an actual pattern shape is predicted from the design data and the predicted shape being set as the reference pattern, it is difficult to predict an actual pattern shape of a recent high-density and complicated pattern accurately, and which causes a problem in which evaluation of the pattern shape is mistaken. Meanwhile PTL 3 discloses the method for evaluating the pattern shape by using a pattern of a good device as a reference pattern, such a single pattern shape does not lead to stable evaluation of the pattern shape when change in pattern shape and generation of edge roughness due to process variation are included in the transferred patterns.

A method for solving these problems is disclosed in PTL 6. In the method in PTL 6, contour distribution data is prepared from contour data of at least two or more circuit patterns, and then a pattern shape is evaluated by using an average shape thereof or a center shape of the contour distribution frame as a reference pattern. However, to prepare the aforementioned contour distribution data, two or more circuit patterns having same exposure conditions and design layouts need to be obtained.

However, the recent semiconductor process has less tolerance for the process variation. For this reason, in the process window analysis in the mass production stage, there is an increased need for using a product pattern, not a pattern prepared for a test. This makes it difficult to obtain two or more circuit patterns having same exposure conditions and design layouts.

Solution to Problem

In order to solve the problem, a device for evaluating a pattern shape of a semiconductor pattern according to the present invention includes: a contour data extraction means for extracting contour data from captured images of a plurality of circuit patterns formed by altering exposure conditions for identical design layouts; a shape change amount measurement means for measuring, on the basis of the plurality of sets of extracted contour data, the amount of shape change at each edge or local region of the circuit patterns; a change amount model computation means for computing, on the basis of the measured amount of shape change, a change amount model for the contour data of a circuit pattern or a shape corresponding to a prescribed exposure condition; and a process window computation means using the change amount model to estimate the amount of shape change of a circuit pattern or a shape corresponding to an arbitrary exposure condition with respect to a circuit pattern or a shape corresponding to an exposure condition specified by a reference exposure condition and compute a process window on the basis of the estimated amount of shape change.

Advantageous Effects of Invention

According to the present invention, a global or local shape difference of a prescribed exposure condition from a reference exposure condition can be computed in high accuracy, and a process window analysis for a prescribed part can be performed in a stable manner. Problems, components, and effects other than those mentioned above are clarified by the following description of embodiments.

DESCRIPTION OF EMBODIMENTS

Hereinbelow will be described a pattern shape evaluation apparatus having a function of specifying a process window in high accuracy by extracting contour data from image data of a plurality of circuit patterns formed under different exposure conditions (a dose amount and a focus value) for identical design layouts and generating, on the basis of the plurality of sets of extracted contour data, the amount of shape change that does not depend on shape change due to process variation. More specifically, an apparatus and a system including as a component a critical dimension scanning electron microscope (CD-SEM), which is a kind of a measurement apparatus, will be described.

Hereinbelow, a charged particle radiation apparatus is illustrated as an example of an apparatus for obtaining image data, and the SEM is described as an embodiment thereof. However, a focused ion beam (FIB) apparatus for obtaining images by scanning a sample with an ion beam may be employed as the charged particle radiation apparatus, for example. However, to measure a miniaturized pattern in high accuracy, extremely high magnification is required, and thus the SEM, which generally exceeds the FIB apparatus in terms of resolution, is preferably used.

(System Configuration)

Figure 1:
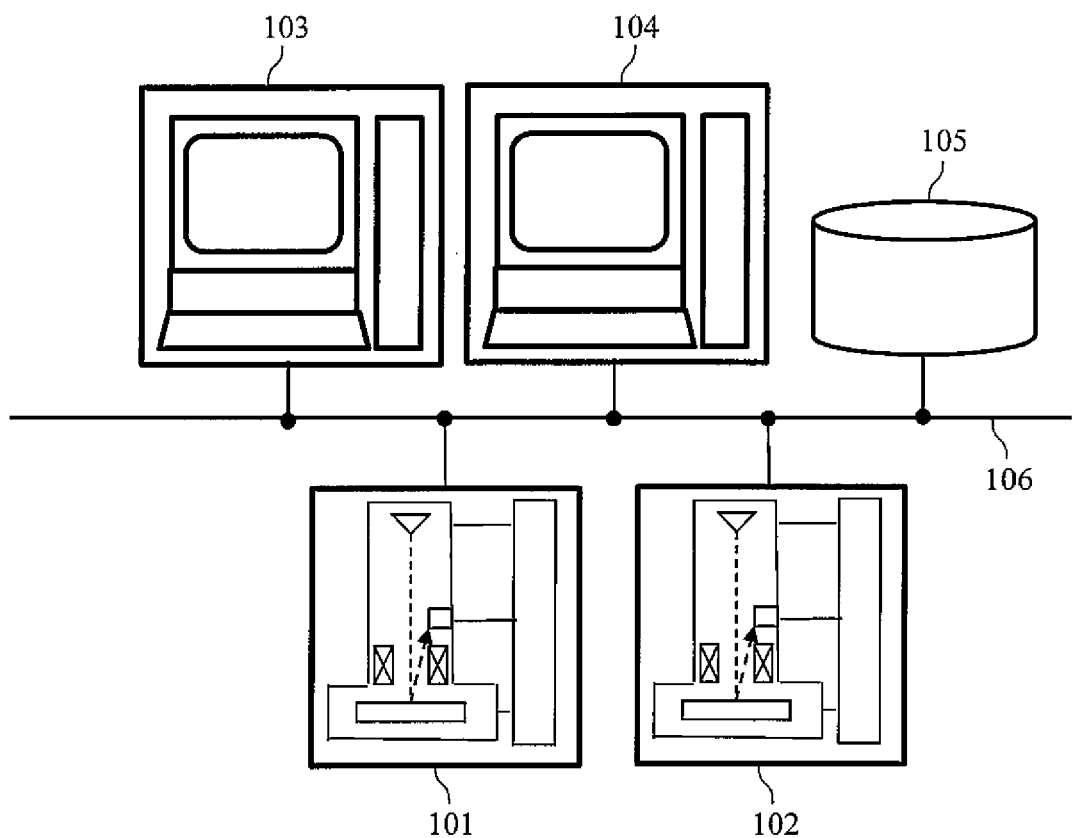
FIG. 1 describes an example of a semiconductor measurement system.

FIG. 1 illustrates a schematic configuration of a semiconductor measurement system in which a plurality of measurement apparatuses and test apparatuses are connected to a network. In the semiconductor measurement system illustrated in FIG. 1, a CD-SEM 101, a defect test apparatus 102, a condition setting apparatus 103, a simulator 104, and a storage medium 105 are connected to a network 106. The CD-SEM 101 is an apparatus for irradiating a sample (a semiconductor wafer, a photomask, or the like) with an electron beam to obtain an image and measuring a pattern dimension from the obtained image. The defect test apparatus 102 is an apparatus for irradiating a sample with an electron beam to obtain an image and extracting a defect on the basis of a comparison result between the obtained image and a reference image recorded in advance. Hereinbelow, each of the CD-SEM 101 and the defect test apparatus 102 is simply referred to as a SEM when the CD-SEM 101 and the defect test apparatus 102 are not distinguished. The condition setting apparatus 103 is an apparatus for setting measurement positions, measurement conditions, and the like on design data of a semiconductor device. The simulator 104 is an apparatus for simulating an outcome of a pattern on the basis of the design data of the semiconductor device and manufacturing conditions and the like of a semiconductor manufacturing apparatus. The storage medium 105 is an apparatus for storing the design data including layout data and manufacturing conditions of the semiconductor device.

The design data is expressed in a GDS format, an OASIS format, or the like and is stored in the storage medium 105 in the prescribed format. It is to be noted that the kind of the design data does not matter as long as software displaying the design data can display the design data in the format, and the design data can be treated as graphic data. Also, the storage medium 105 may be built in a control unit of the CD-SEM 101, a control unit of the defect test apparatus 102, the condition setting apparatus 103, or the simulator 104. Meanwhile, each SEM is provided with a not-illustrated control unit, which executes control required for the SEM. Each control unit may have a function of the simulator 104 and a function of setting measurement conditions and the like.

The SEM focuses an electron beam emitted from an electron source with use of a multistage lens and thereafter deflects the electron beam and scans with use of a scanning deflector. In this manner, the electron beam scans on the surface of a sample one-dimensionally or two-dimensionally. Secondary electrons (SE) or backscattered electrons (BSE) emitted from the surface of the sample by scanning of the electron beam are detected by a detector and are stored in a storage medium such as a frame memory in sync with scanning with use of the scanning deflector. An image signal stored in the frame memory is accumulated by a computing unit built in the control unit. The scanning deflector can scan in an arbitrary size at an arbitrary position in an arbitrary direction. The above control and the like are executed by the control unit of the SEM. The image and the corresponding signal obtained by scanning of the electron beam are transmitted to the condition setting apparatus 103 via the network 106.

In the present embodiment, the control unit of each SEM and the condition setting apparatus 103 are separate units. However, the condition setting apparatus 103 may control each SEM, or the control unit of each SEM may execute condition setting processing. The condition setting apparatus 103 or the control unit of each SEM has stored therein a program for executing measurement processing and executes measurement or computation in accordance with the program.

The condition setting apparatus 103 is provided with a function of preparing a program (recipe) for controlling operation of the SEM on the basis of the design data of the semiconductor device and functions as a recipe setting unit. Specifically, the condition setting apparatus 103 sets positional information (e.g., a measurement point, an auto-focus point, an auto astigmatism point, and an addressing point on the design data, contour data of a pattern, and the simulated design data) and the like for making the SEM execute necessary processing and prepares a program for automatically controlling a sample stage, the deflector, and the like of the SEM on the basis of the setting. The condition setting apparatus 103 also has built or stored therein a program for causing a dedicated or general-purpose processor to extract information in a region for a template from the design data and prepare the template on the basis of the extracted information.

(Configuration of Scanning Electron Microscope)

Figure 2:
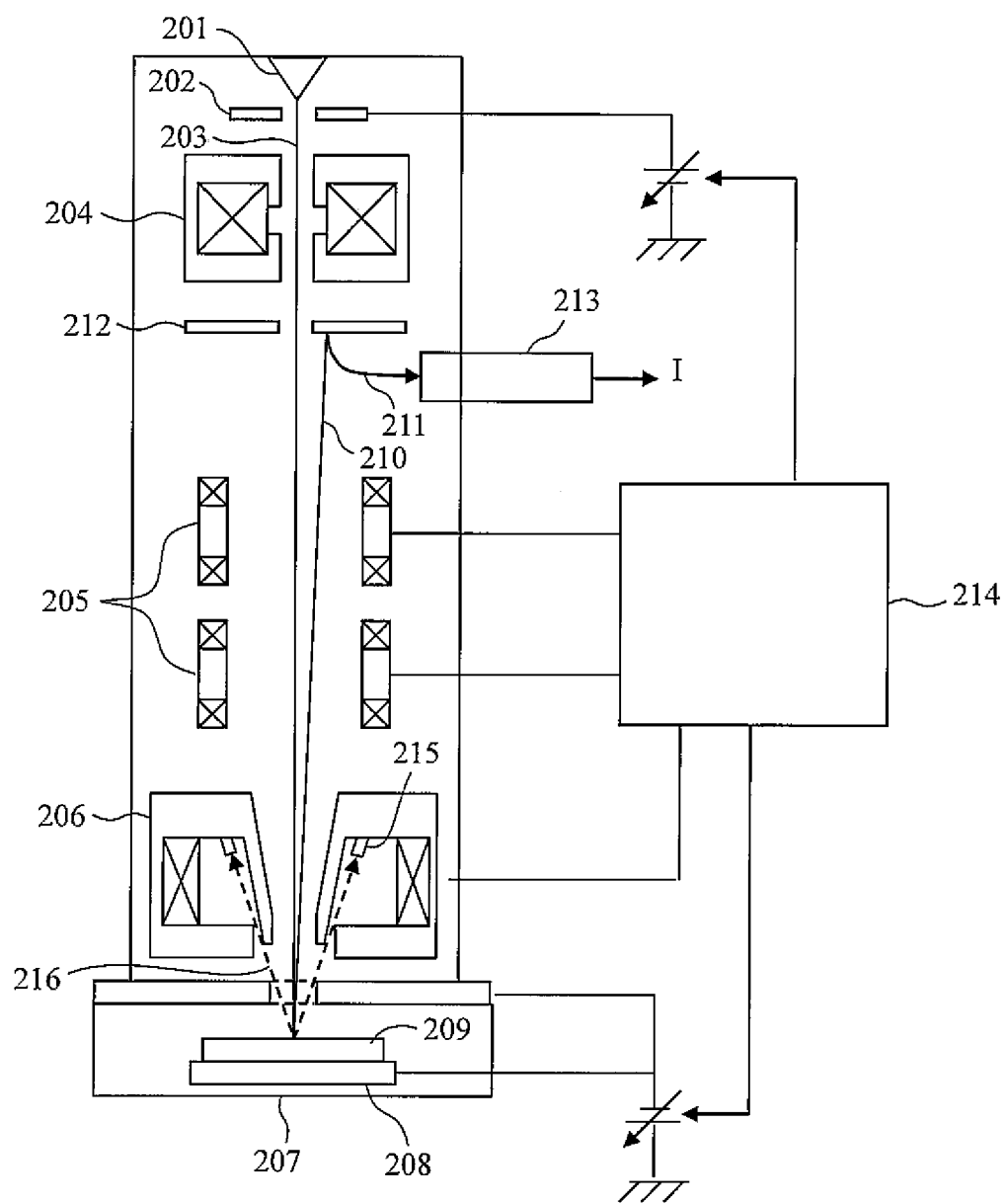
FIG. 2 illustrates a schematic configuration example of a scanning electron microscope.

FIG. 2 illustrates a schematic configuration example of the scanning electron microscope. An electron beam 203 is extracted from an electron source 201 by an extraction electrode 202 and is accelerated by a not-illustrated acceleration electrode. The accelerated electron beam 203 is focused by a condenser lens 204 as an example of a focusing lens and is thereafter deflected by a scanning deflector 205. Accordingly, the electron beam 203 scans on a sample 209 one-dimensionally or two-dimensionally. The electron beam 203 incident in the sample 209 is decelerated by negative voltage applied to an electrode built in a sample stage 208, and is focused due to a lens effect of an objective lens 206 to irradiate a surface of the sample 209. Electrons 210 (secondary electrons, backscattered electrons, or the like) are emitted from the irradiated part on the sample 209. The emitted electrons 210 are accelerated in a direction of the electron source 201 due to an acceleration effect caused by the negative voltage applied to the electrode built in the sample stage 208. The accelerated electrons 210 collide with a conversion electrode 212 to generate secondary electrons 211. The secondary electrons 211 emitted from the conversion electrode 212 are trapped by a detector 213; an output I of the detector 213 changes depending on the amount of the trapped secondary electrons. Luminance of a not-illustrated display unit changes depending on the change of the output I. For example, when a two-dimensional image is formed, a deflection signal to the scanning deflector 205 and the output I of the detector 213 are synchronized to form an image in a scanning region. Meanwhile, in the scanning electron microscope in FIG. 2, an electron detector 215 detecting the secondary electrons 216 is arranged in the objective lens 206.

Although FIG. 2 shows a configuration example in which the electrons 210 emitted from the sample 209 are once converted into the secondary electrons 211 by the conversion electrode 212 and the secondary electrons 211 are detected, the present invention is not limited to this configuration. For example, a configuration in which an electron multiplier or a detection surface of the detector is arranged on the orbit of the accelerated electrons may be employed. A control unit 214 has a function of forming an image on the basis of the detected electrons and a function of measuring a pattern width of a pattern formed on the sample on the basis of an intensity distribution of the detected electrons, called a line profile, as well as a function of controlling respective components of the scanning electron microscope.
(Configuration of Pattern Shape Evaluation Apparatus)

Next, a configuration example of a pattern shape evaluation apparatus will be described. The pattern shape evaluation apparatus is realized through an image evaluation processing: (1) the processing is built in the control unit 214; (2) the processing is provided by image processing of a computing unit in the control unit 214; or (3) the processing is provided by an external computing unit (e.g., the condition setting apparatus 103) connected to the control unit 214 via the network, for example.

Figure 3:
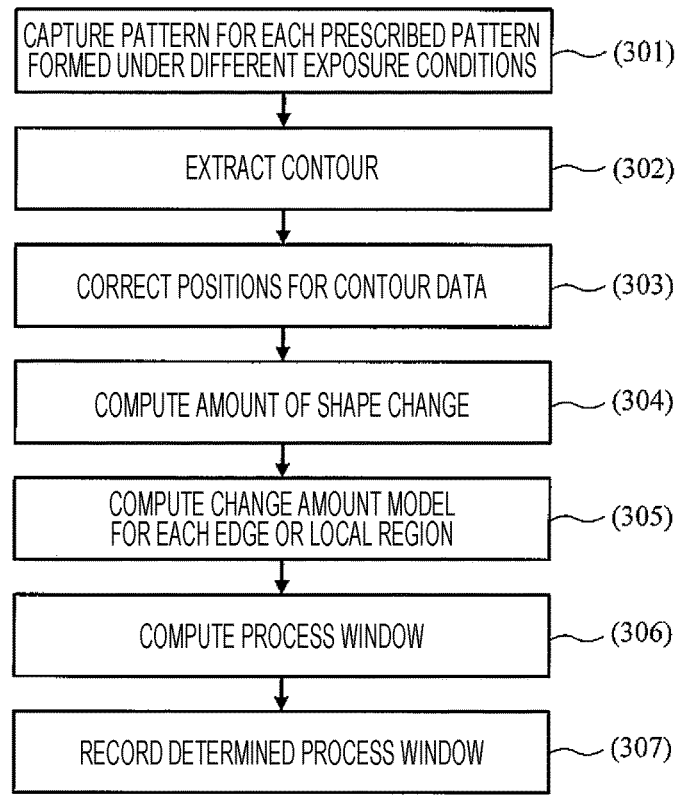
FIG. 3 is a flowchart illustrating an evaluation method performed by a pattern shape evaluation apparatus.

FIG. 3 illustrates evaluation processing performed by the pattern shape evaluation apparatus according to an embodiment. This evaluation processing includes: (1) processing for generating contour data on the basis of a SEM image captured by the aforementioned scanning electron microscope; (2) processing for generating a shape change model (hereinbelow referred to as "a change amount model") on the basis of the generated contour data; and (3) processing for setting and recording a process window with use of the generated change amount model (circuit pattern).

First, the pattern shape evaluation apparatus captures as SEM images an FEM (focus exposure matrix) wafer on which identical circuit patterns are printed by changing an exposure condition (the dose amount and the focus value) per shot (each exposure) (301). Meanwhile, a SEM image having a collapsed pattern is not suitable for preparation of a model. For this reason, the SEM image having the collapsed pattern may be removed at this time in advance.

Subsequently, the pattern shape evaluation apparatus respectively extracts contours of the circuit patterns from the respective SEM images (302). Various methods for extraction of contours are proposed, and a method disclosed in PTL 7 (Publication of JP 2006-66478 A) and the like or a method disclosed in NPL 1 "R. Matsuoka, New method of Contour based mask shape compiler, SPIE Proc 6730-21, 2007.9.21" can be applied, for example.

Figure 4A:
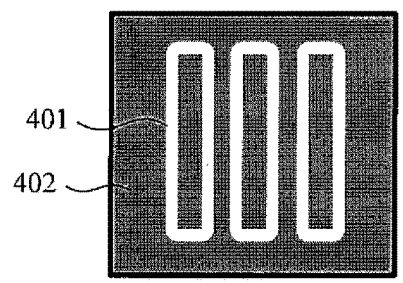
FIGS. 4A and 4B illustrate a captured image of a pattern and contour data of the pattern extracted from the captured image.
Figure 4B:
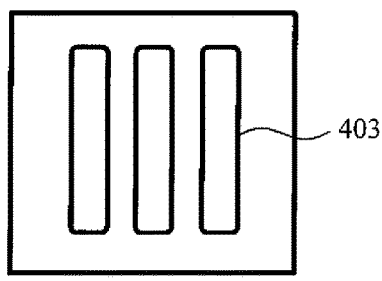

When the circuit pattern is captured by the SEM, an inclined part or a protruded part of the circuit pattern is imaged as a white strip-like image (a white strip image 401) as illustrated in FIG. 4(a). The pattern shape evaluation apparatus applies the method in PTL 7 or NPL 1 to a SEM image 402 including this white strip image 401 and extracts lined contour data 403 as in FIG. 4(b). Generation of the contour data 403 is executed for all the SEM images 402 except the aforementioned collapsed pattern.

Figure 5:
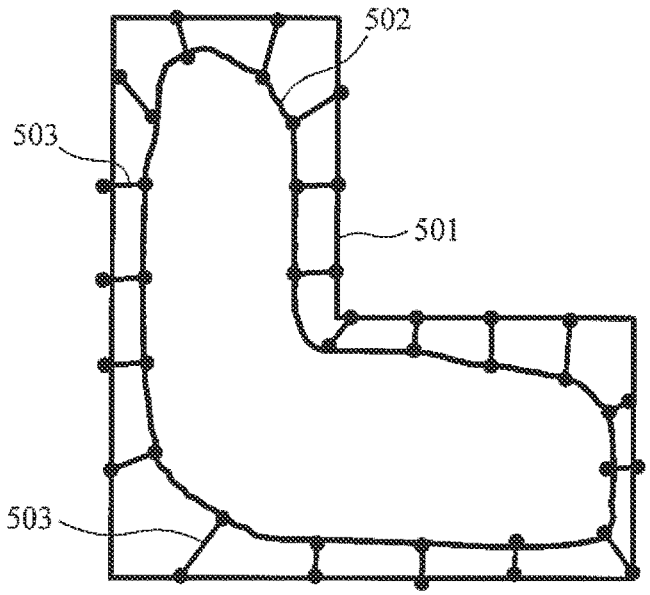
FIG. 5 describes an inter-edge distance between the contour data and design data.

Subsequently, as preprocessing before measurement of the amount of shape change, the pattern shape evaluation apparatus executes position correction between the contour data as illustrated in FIG. 5 to improve accuracy of the measurement value (303). At this time, the pattern shape evaluation apparatus selects design data 501 (FIG. 5) or representative contour data, measures inter-edge distances 503 from corresponding contour data 502, and computes positions at which the measured values are the lowest and at which the variation is the least. Meanwhile, when the exposure condition is out of an optimal value, local shape change may occur, variation may be generated in the center positions and the inter-edge distances 503, and position correction may not be performed correctly in the entire circuit pattern. Under such circumstances, the present embodiment copes with the local shape change caused by the change in the exposure condition to execute position correction.

Figure 6:
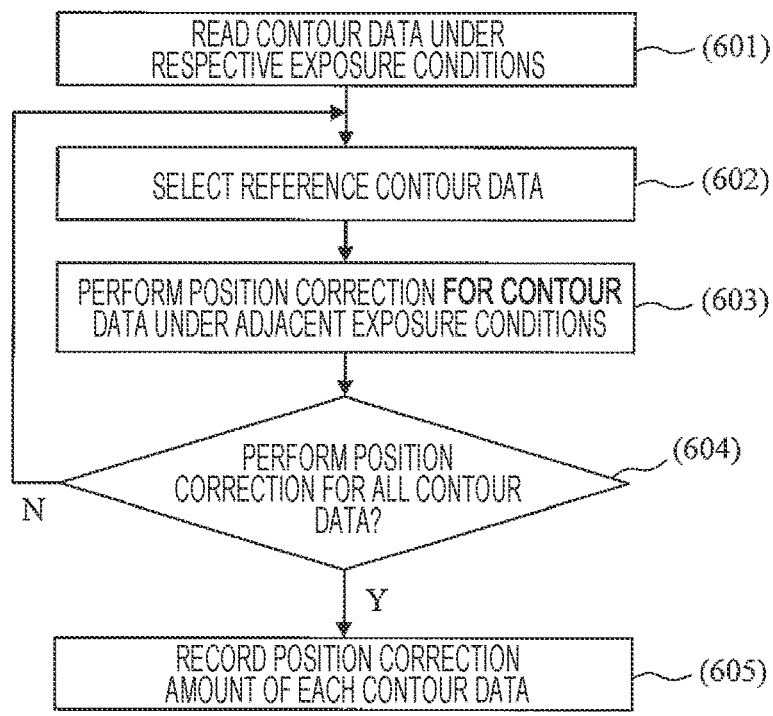
FIG. 6 is a flowchart illustrating a local position correction method of the contour data.

FIG. 6 illustrates position correction processing of the contour data on the assumption of the local shape change caused by the change in the exposure condition. For the position correction, the pattern shape evaluation apparatus first reads the contour data from the SEM images corresponding to the respective exposure conditions (601). Subsequently, the pattern shape evaluation apparatus selects reference contour data (602). As the reference contour data, contour data 701 (FIG. 7) giving a median is selected from among the plurality of contour data corresponding to the respective exposure conditions, for example. In the present description, the contour data giving the median is referred to as "reference contour data," and an exposure condition used to form the reference contour data is referred to as "a reference exposure condition." The circuit pattern corresponding to the reference contour data is not necessarily at a center position of the FEM wafer.

Figure 7:
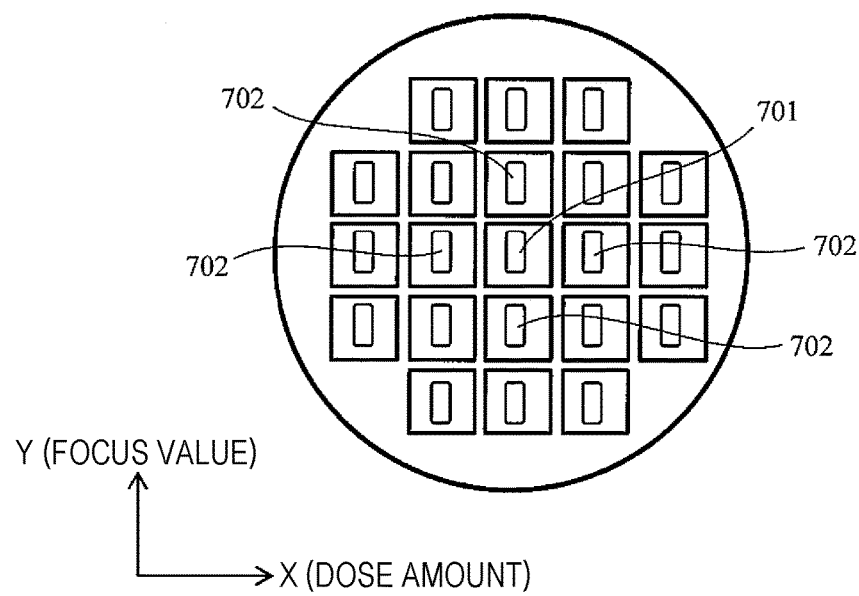
FIG. 7 illustrates relationship between each shot on an FEM wafer and an exposure condition used to form the shot.
Figure 8A:
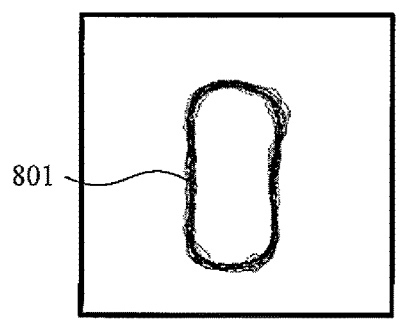
FIGS. 8A-8E illustrate an example of a measurement method of the amount of shape change.
Figure 8B:
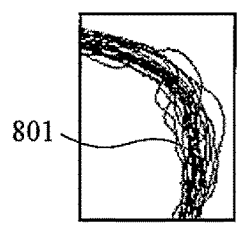
Figure 8C:
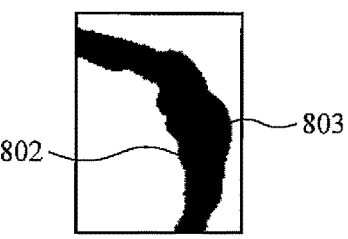
Figure 8D:
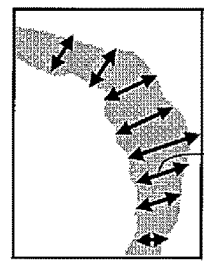
Figure 8E:
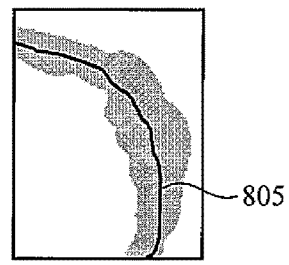

FIG. 7 illustrates relationship between the exposure conditions and the corresponding contour data. FIG. 7 is an entire image of the aforementioned FEM wafer. It is supposed that the dose amount of each shot arranged in the wafer in a matrix form is larger on the right side in a horizontal direction and smaller on the left side; the focus value of each shot is larger on the upper side in a vertical direction and is smaller on the lower side.

Subsequently, the pattern shape evaluation apparatus derives the inter-edge distances between the reference contour data (contour data 701) and contour data 702 obtained from the SEM images of the circuit data formed under different exposure conditions adjacent to the exposure condition corresponding to the reference contour data, and performs position correction for the contour data so that the respective edges may be located at positions at which the distances are the lowest and at which the variation is the least (603). Examples of a method for computing the positions at which the inter-edge distances are the lowest and at which the variation is the least are a method for deriving a root mean square from the inter-edge distances of the entire contour data and deriving positions at which the values are the lowest while shifting the patterns to be corrected and a method for computing positions at which the root mean square is minimized by means of a least-square method.

Subsequently, the pattern shape evaluation apparatus sets the contour data in which the position correction has been completed as new reference contour data and repeats the processing until all the position correction operations are completed (604). The pattern shape evaluation apparatus finally records the position correction amount of the contour data under each exposure condition on a memory or in a file (605). Consequently, positional relationship among the contour data under adjacent exposure conditions can be specified.

Description of FIG. 3 is resumed. After completion of the correction processing, the pattern shape evaluation apparatus measures the amount of shape change of each contour data (304). For measurement of the amount of shape change, the method disclosed in PTL 3 (Publication of JP 10-312461 A) or PTL 6 (Publication of JP 2009-194051 A) is applied, for example. This method is a method for identifying or generating a reference pattern and measuring a distance from another contour data.

In modeling the amount of shape change to generate a virtual shape, the virtual shape needs to be defined so that the measurement directions of the respective successive edges may be successive and smooth without intersecting with each other. Therefore, as illustrated in FIGS. 8(*a*) to 8(*e*), the pattern shape evaluation apparatus extracts minimum contour data (innermost contour data) 802 and maximum contour data (outermost contour data) 803 from overlapping data 801 of the respective contour data and makes the two contour data correspond to each other so that the edges of the two contour data may change smoothly and may not intersect with each other (derives corresponding relations 804), for example. Alternatively, the pattern shape evaluation apparatus derives medians 805 between the minimum contour data 802 and the maximum contour data 803 and controls vector directions so that a normal vector of a median may not intersect with a normal vector of an adjacent median within a range from the minimum contour data 802 to the maximum contour data 803. After this measurement, the pattern shape evaluation apparatus derives the amount of shape change of each contour data on the basis of the defined measurement directions.

Figure 9:
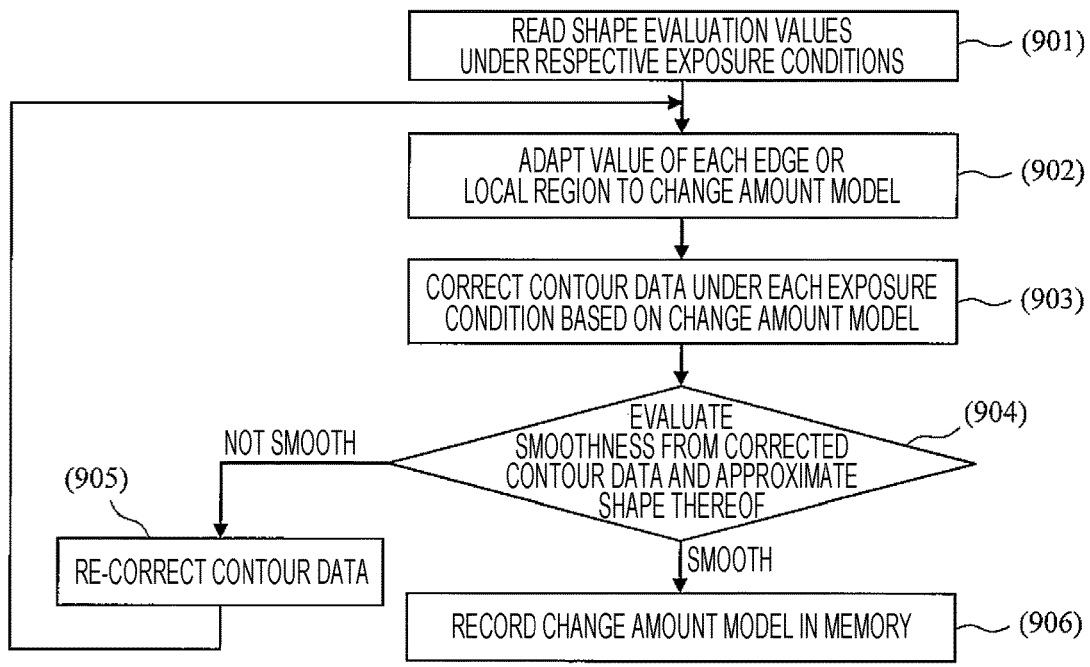
FIG. 9 is a flowchart illustrating an example of a generation method of a change amount model.
Figure 10:
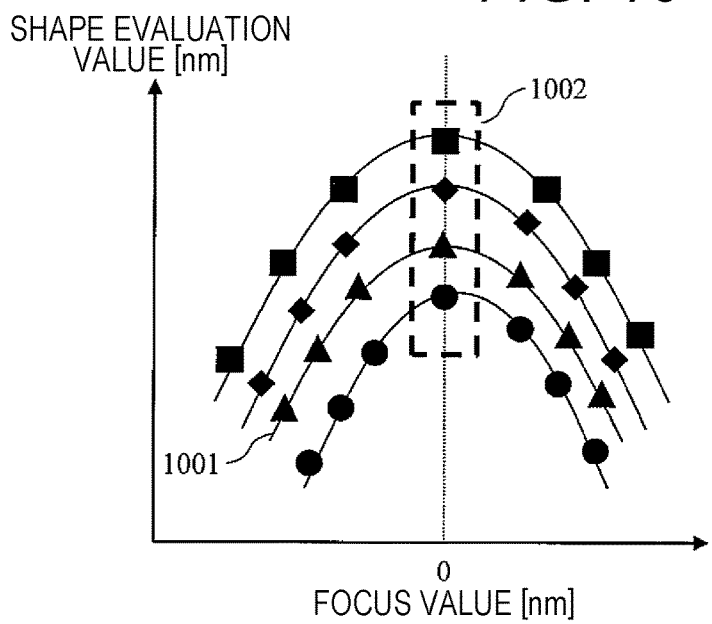
FIG. 10 illustrates the change amount model for each edge.

Description of FIG. 3 is resumed. The pattern shape evaluation apparatus generates the change amount model for each edge or local region on the basis of the measured change amount (305). FIG. 9 illustrates processing for generating the change amount model. Note that the change amount measured for each edge or local region does not have an ideal value because of change in pattern shape and generation of edge roughness due to process variation. The ideal value means the amount of shape change conforming to generally known physical characteristics. For example, when the dose amount is constant while only the focus value is changed, a shape evaluation value shifts to match a quadratic curve (1001 in FIG. 10). Also, when the focus value is constant while only the dose amount is changed, the shape evaluation value shifts to match a line or a logarithmic approximation curve (1002 in FIG. 10). A model created by formulating the relationship between the focus value and the dose amount is called as the change amount model.

The pattern shape evaluation apparatus first reads the shape evaluation values under the respective exposure conditions (901) and adapts the measurement value of each edge or local region to the change amount model (902) to correct each contour data (903). Since correction of the contour data is performed independently for each edge, smoothness of the corrected contour data is lost. The pattern shape evaluation apparatus evaluates smoothness of the corrected contour data (904), and when the corrected contour data is not smooth, the contour data is re-corrected by shape approximation (905). After the re-correction, the pattern shape evaluation apparatus adapts information of each edge of the corrected contour data to the change amount model again and repeats processing until the adaptation to the change amount model and the smoothness of the contour data reach prescribed values. When it is confirmed that the contour data is smooth, the pattern shape evaluation apparatus records the computed change amount model in a memory (906). By using the generated change amount model, the contour data can be generated under an arbitrary exposure condition that is not limited to the exposure conditions used for generating the change amount model (that is, the exposure conditions used for generating the FEM wafer), and that is not depending on within or out of the range of these exposure conditions. Meanwhile, the contour data corresponding to an exposure condition within the range of the exposure conditions used for generating the change amount model is computed by interpolation calculation among the contour data corresponding to adjacent exposure conditions. Also, the contour data corresponding to an exposure condition out of the range of the exposure conditions used for generating the change amount model is computed by extrapolation calculation among the contour data corresponding to adjacent exposure conditions.

Description of FIG. 3 is resumed. The pattern shape evaluation apparatus uses the computed change amount model to derive a plurality of amounts of shape change between a pattern shape generated under a prescribed optimal exposure condition and contour data generated under arbitrary exposure conditions, estimates the amounts of shape change from ideal contour data under the exposure conditions, and computes a process window on the basis of the estimated amounts of shape change (306). The computation of the process window does not need to be based on the entire pattern shape but can be performed for each arbitrary part (e.g., an edge). The pattern shape evaluation apparatus then records the computed process window in a memory or the like (307).

(Summary)

As described above, according to the present embodiment, on the basis of SEM images of a plurality of circuit patterns having identical design layouts and different exposure conditions, ideal pattern shapes corresponding to the respective exposure conditions can be generated. Accordingly, a global or local shape difference of a different exposure condition can be computed from a prescribed exposure condition in high accuracy, and a process window analysis for a prescribed part can be performed in a stable manner.

(Other Embodiments)

It is to be noted that the present invention is not limited to the above embodiments and includes various modification examples. For example, each of the above embodiments is just an illustrative embodiment described in detail to facilitate understanding of the present invention, and the present invention does not always need to include all the components and processing described here. Also, other components and processing may be added to each of the above embodiments, or partial components and processing in each of the above embodiments may be deleted or substituted.

Also, the aforementioned respective components, functions, processing units, processing means, and the like may partially or entirely be fulfilled as hardware such as an integrated circuit. The aforementioned respective components, functions, and the like may also be fulfilled by making a processor interpret and execute programs fulfilling the respective functions. That is, they may be fulfilled as software. Data for fulfilling the respective functions such as programs, tables, and files can be stored in a storage unit such as an SSD (solid state drive) and a storage medium such as an IC card, an SD card, and a DVD.

Also, the control lines and data lines considered as necessary in the description have been shown, and not all the control lines and data lines required for a product are shown. Almost all of the components may be considered as being connected to each other in practice.

REFERENCE SIGNS LIST

101 CD-SEM
102 defect test apparatus
103 condition setting apparatus
104 simulator
105 storage medium
106 network
201 electron source
202 extraction electrode
203 electron beam
204 condenser lens
205 scanning deflector
206 objective lens
207 stage
208 sample stage
209 sample
210 emitted electron
211 secondary electron
212 conversion electrode
213 detector
214 control unit
215 electron detector
216 secondary electron

The invention claimed is:

1. A pattern shape evaluation device comprising:
    a contour data extraction means for extracting contour data from captured images of a plurality of circuit patterns formed by altering exposure conditions for identical design layouts;
    a shape change amount measurement means for measuring, on the basis of the plurality of sets of extracted contour data, the amount of shape change at each edge or local region of the circuit patterns;
    a change amount model computation means for computing, on the basis of the measured amount of shape change, a change amount model for the contour data of a circuit pattern or a shape corresponding to a prescribed exposure condition; and
    a process window computation means using the change amount model to estimate the amount of shape change of a circuit pattern or a shape corresponding to an arbitrary exposure condition with respect to a circuit pattern or a shape corresponding to an exposure condition specified by a reference exposure condition and compute a process window on the basis of the estimated amount of shape change.

2. The pattern shape evaluation apparatus according to claim 1, further comprising;
    a contour data position correction means for, with the plurality of sets of contour data extracted by the contour data extraction means set as targets to be processed, performing position correction among the contour data extracted from the captured images of the circuit patterns whose exposure conditions are adjacent to each other.

3. The pattern shape evaluation apparatus according to claim 1, wherein the change amount model computation means adapts the measured amount of shape change to the change amount model for each edge to correct the contour data extracted from the captured images corresponding to the respective exposure conditions.

4. The pattern shape evaluation apparatus according to claim 3, wherein the change amount model computation means determines smoothness of the corrected contour data and re-corrects the contour data by shape approximation when the contour data is determined not to be smooth.

5. The pattern shape evaluation apparatus according to claim 1, wherein the process window computation means computes the process window for an arbitrary part of the circuit pattern with use of the change amount model.

6. A pattern shape evaluation method comprising:
    first processing for extracting contour data from captured images of a plurality of circuit patterns formed by altering exposure conditions for identical design layouts;
    second processing for measuring, on the basis of the plurality of sets of extracted contour data, the amount of shape change at each edge or local region of the circuit patterns;
    third processing for computing, on the basis of the measured amount of shape change, a change amount model for the contour data of a circuit pattern or a shape corresponding to a prescribed exposure condition; and
    fourth processing for estimating, with use of the change amount model, the amount of shape change of a circuit pattern or a shape corresponding to an arbitrary exposure condition with respect to a circuit pattern or a shape corresponding to an exposure condition specified by a reference exposure condition, computing a process window on the basis of the estimated amount of shape change.

7. The pattern shape evaluation method according to claim 6, further comprising;
    processing for setting the plurality of sets of contour data extracted in the first processing as targets to be processed, performing position correction among the contour data extracted from the captured images of the circuit patterns whose exposure conditions are adjacent to each other.

8. The pattern shape evaluation method according to claim 6, wherein the third processing adapts the measured amount of shape change to the change amount model for each edge to correct the contour data extracted from the captured images corresponding to the respective exposure conditions.

9. The pattern shape evaluation method according to claim 8, wherein the third processing determines smoothness of the corrected contour data and re-corrects the contour data by shape approximation when the contour data is determined not to be smooth.

10. The pattern shape evaluation method according to claim 6, wherein the fourth processing computes the process window for an arbitrary part of the circuit pattern with use of the change amount model.

* * * * *